United States Patent [19]
Lee

[11] Patent Number: 6,146,399
[45] Date of Patent: Nov. 14, 2000

[54] TISSUE CUTTING CLAMP APPARATUS

[76] Inventor: Scott S. Lee, 6 Sandbridge, Aliso Viejo, Calif. 92656

[21] Appl. No.: 08/946,864

[22] Filed: Oct. 8, 1997

[51] Int. Cl.[7] ............................................ A61B 17/32
[52] U.S. Cl. ........................ 606/167; 606/205; 30/124
[58] Field of Search ............................ 606/205, 207, 606/170, 137, 120, 167; 30/329, 124

[56] References Cited

U.S. PATENT DOCUMENTS

| | | | |
|---|---|---|---|
| 2,679,249 | 5/1954 | Weihmann | 30/124 |
| 5,749,893 | 5/1998 | Vidal et al. | 606/205 |

*Primary Examiner*—Michael Buiz
*Assistant Examiner*—Tan-Uyen T. Ho
*Attorney, Agent, or Firm*—Edward E. Roberts

[57] ABSTRACT

Hand manipulable tissue cutting apparatus formed in a scissors like configuration and having first and second clamp members pivotably coupled with first and second jaws in opposing facing interoperative relation. On at least one clamp member surface a plane is defined at the area of the jaws, the plane being generally perpendicular to the opposing abutting faces of the jaws. A sheath is provided of a first sheath portion attached, or formed integrally with a first clamp member, and a second sheath portion attached or formed integrally with the second clamp member. In the closed clamp position, the first and second sheath portions form generally parallel guide recesses. A blade member is provided with a width and thickness sufficient for sliding within the guide recesses so-formed. In the open position of the clamp, the first sheath portion integral with the first clamp member is configured for retaining the blade in its retracted position. A spring biased latch strip is attached on one end to the first clamp member, with the other end of the latch strip having a projection for engaging a detent in the side edge of the blade with the blade retracted. Means are provided on the first clamp member for precluding unintentional withdrawal of the blade. In operation the tissue is clamped, after which the blade is pushed forward (relative to the operator position) for cutting the so-clamped tissue. In an alternative embodiment, the jaws are adjustable to enable only partial cutting of the clamped tissue or body part.

20 Claims, 13 Drawing Sheets

TISSUE CUTTING CLAMP APPARATUS

BACKGROUND OF THE INVENTION

1. Field of the Invention

This invention relates to surgical devices, and more particularly to a tissue cutting clamp.

2. Description of the Prior Art

Surgical clamps are extensively used in surgery, with such clamps taking the general form of a pair of scissors, minus blades, with the ends configured with opposing flat and/or serrated faces for gripping a portion of tissue or other bodily organ or component. Such surgical clamps are often provided with interlocking members adjacent the finger gripping openings for providing the clamping action.

Such clamps are often used for securing a body or tissue part prior to cutting, such as in a hysterectomy operation, or severing of a nerve or blood vessel. One prior art blade holder is shown and described in U.S. Pat. No. 2,679,249 entitled Instrument for Surgical Operations issued to WEIHMANN on 25 May 1954, the pliers-like instrument providing for clamping and severing tissue with the inside opposing faces of the jaws of the instrument having grooves for slidably holding a blade mounted for longitudinal movement for cutting during surgery.

A Retractable Surgical Knife is shown and described in U.S. Pat. No. 5,292,329, issued to WERNER on 8 Mar. 1994, the knife including latch means for releasably locking the blade in an operative position.

Dissector-Obstructor Apparatus is shown and described in U.S. Pat. No. 3,175,556, issued to WOOD et al. on 26 Jul. 1960, the scissors-like apparatus providing for clamping and severing tissue and including latch means for releasably locking the blade in an operative position.

In accordance with a feature of the present invention, there is provided a new and improved tissue cutting blade with the blade operable in a plane adjacent or overriding the plane of one surface of the engaged jaws.

SUMMARY OF THE INVENTION

The foregoing and other objects of the invention are accomplished by providing a hand manipulable tissue cutting clamp apparatus formed in a scissors-like configuration and having first and second clamp members pivotably coupled with first and second jaws in opposing facing interoperative relation. The clamp members, on at least one surface thereof, define a plane at the area of the jaws, with this plane being generally perpendicular to the opposing abutting faces of the jaws.

A sheath is provided of a first sheath portion attached, or formed integrally with a first clamp member and a second sheath portion attached or formed integrally with the second clamp member. In the closed position of the clamp, the first and second sheath portions form guide recesses which are generally parallel to one another. A knife or blade member is provided with a width and thickness sufficient for closely sliding with the guide recesses so-formed.

In the open position of the clamp, the first sheath portion affixed to or integral with the first clamp member is configured for retaining the blade in its retracted position, that is with the blade withdrawn toward the finger gripping handle openings. A spring biased latch strip is attached on one end to the first clamp member, with the other end of the latch strip having a projection for engaging a detent in the side edge of the blade with the blade retracted. The first clamp also is provided with a blade stop member at the retracted position of the blade for precluding unintentional withdrawal of the blade.

The opposite side edge of the blade is provided with generally right-angularly oriented guide legs for engaging a guide channel formed in the face of the first clamp at the jaw area. In operation, the tissue is clamped, after which the blade is pushed forward (relative to the operator position) for cutting the so-clamped tissue.

Other objects, features and advantages of the invention will become apparent on a reading of the specification when taken in conjunction with the drawings in which like reference numerals refer to like elements in the several views.

DESCRIPTION OF THE PREFERRED EMBODIMENT

Figure 1:
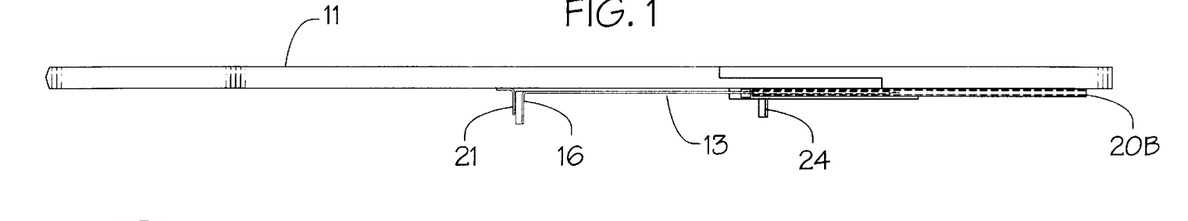
FIG. 1 is a perspective view of a first embodiment of the tissue cutting clamp apparatus according to the invention.
Figure 2:
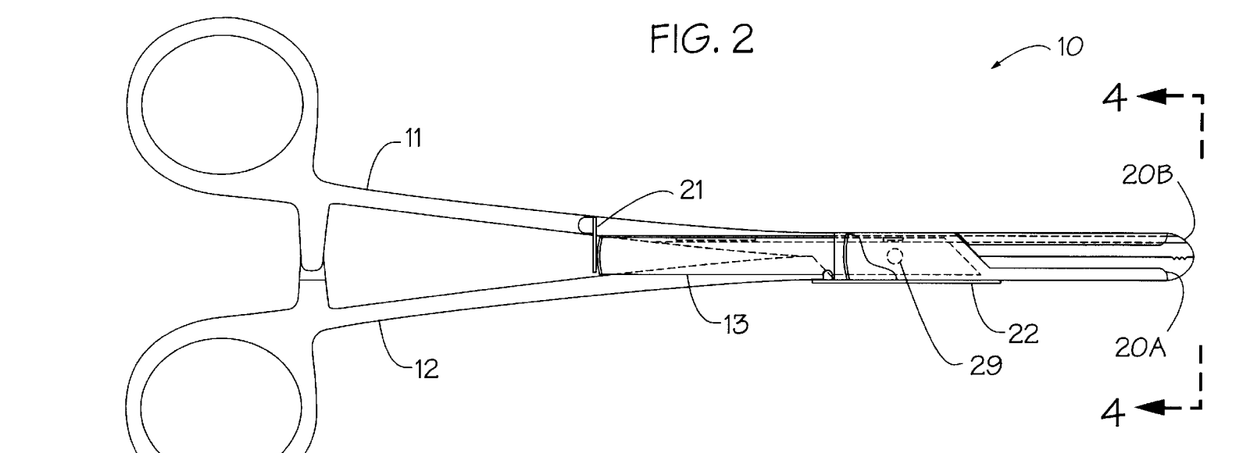
FIG. 2 is an exploded perspective view of the tissue cutting clamp apparatus of FIG. 1 with the blade in its removed position.
Figure 3:
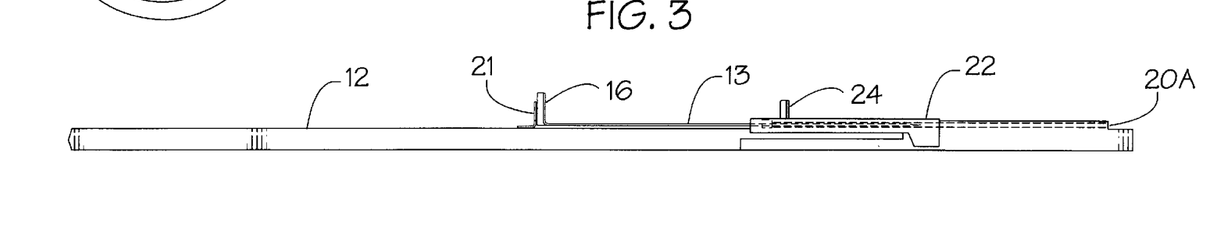
FIG. 3 is an exploded perspective view of the tissue cutting clamp apparatus of FIG. 1 with the blade inserted into the retention sheath portion of the first clamp member.

Referring now to the drawings and particularly to FIGS. 1 through 3, there is shown a tissue cutting clamp apparatus, generally designated 10, formed of first and second clamp members, generally designated 11 and 12, which as will be described, are configured for slidable retention of a blade 13 (See FIG. 2).

The blade 13 is generally planar and of elongate generally rectangular strip form with a canted or angular knife edge 15 at one end and a bent handle portion 16 at the other end, these ends being at opposite ends of the long axis of the blade 13. For reasons hereafter described, one side edge of the blade 13 is provided with a detent or notch 14 (as viewed in FIG. 2) and the opposite long edge is provided with first and second downwardly depending guide legs 17 and 18 which are in a common plane, generally perpendicular to the plane of the blade 13.

The first clamp member 11 is provided, at one end, with a finger gripping opening 11A, and clamp member 12 is likewise provided with a like formed mirror image finger gripping opening 12A. Adjacent the finger gripping openings 11A and 12A, clamp members 11 and 12 are provided with ramped serrated projection members 11B and 12B which interlock for clamping purposes as is conventional with surgical clamps.

The first and second clamp members 11 and 12 are assembled in the form of a pair of scissors or forceps (See FIGS. 2 and 3), with first and second jaw areas 11C and 12C being at the ends of the clamp members 11 and 12 opposite the finger gripping openings 11A and 12A. The clamp members 11 and 12 are pivotable about an axis defined by projection 29 passing through an aperture of clamp member 12 for retention by coupler or fastener clip 29A.

Briefly, as will be described, the first clamp member 11 has provision for retaining the blade 13 therein and for axial sliding movement of the blade along the adjacent generally planar surfaces of the facing jaw areas 11C and 12C, with the first clamp member 11 being able to retain the blade 13 independently of the clamp member 12, as will be described. In addition, the movement of the blade is along an axial line extending generally along a slight angle to the long axis of the first clamp member 11 (excluding the offset finger gripping opening 11A). The advantages of this construction will become apparent.

Referring to FIGS. 2 and 3, the first clamp member 11 has an integrally formed guide channel 19 formed as a recess in a slit 20 formed in a sheath member 20A, which, as shown, has a portion thereof forming a shroud adjacent the pivot axis 29 and a portion forming a blade guide rail adjacent the clamping jaw area 11C, the blade guide rail portion having a length slightly less than the length of the jaw for non-interference during clamping.

Figure 4:
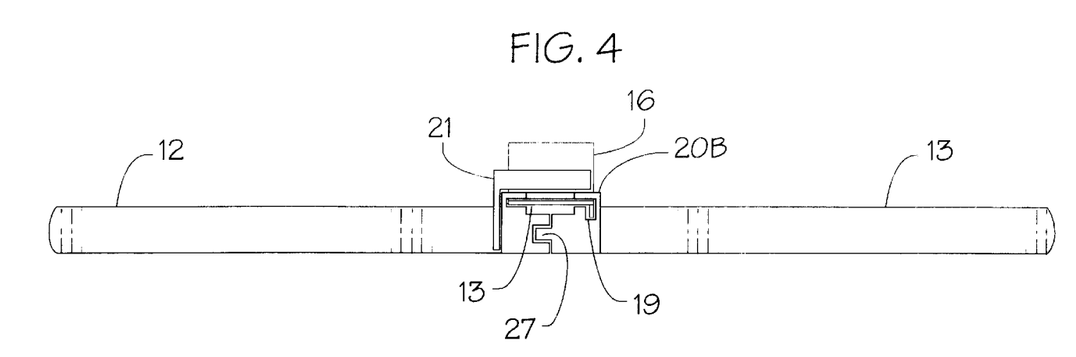
FIG. 4 is a plan view of the tissue cutting clamp apparatus of FIG. 1 with the blade in its operative position with the jaws thereof in the closed position.

Guide channel 19 is configured, dimensioned and arranged to slidingly receive blade guides 17 and 18 as blade 13 is moved fully forward as shown in FIGS. 3 and 4.

The second clamping member 12 includes a second sheath portion in the form of a blade guide rail 20B which is of similar configuration and length to the guide rail portion of the sheath 20A, the open edges of the blade guide rails of sheaths 20A and 20B being in facing aligned relation and having a height dimension slightly greater than the thickness of the blade 13. Also formed in the jaw area of the second clamping member 12 is a guide channel portion 19A configured, dimensioned and arranged to be in alignment with the guide channel 19 of the first clamping member 11 and to slidingly receive blade guides 17 and 18 as blade 13 is moved fully forward with the jaws fully closed.

Thus, when the jaws are closed in the cutting position, blade 13 is guided through the guide rails with blade guides 17 and 18 being constrained sequentially by channels 19 and 19A.

Figure 14:
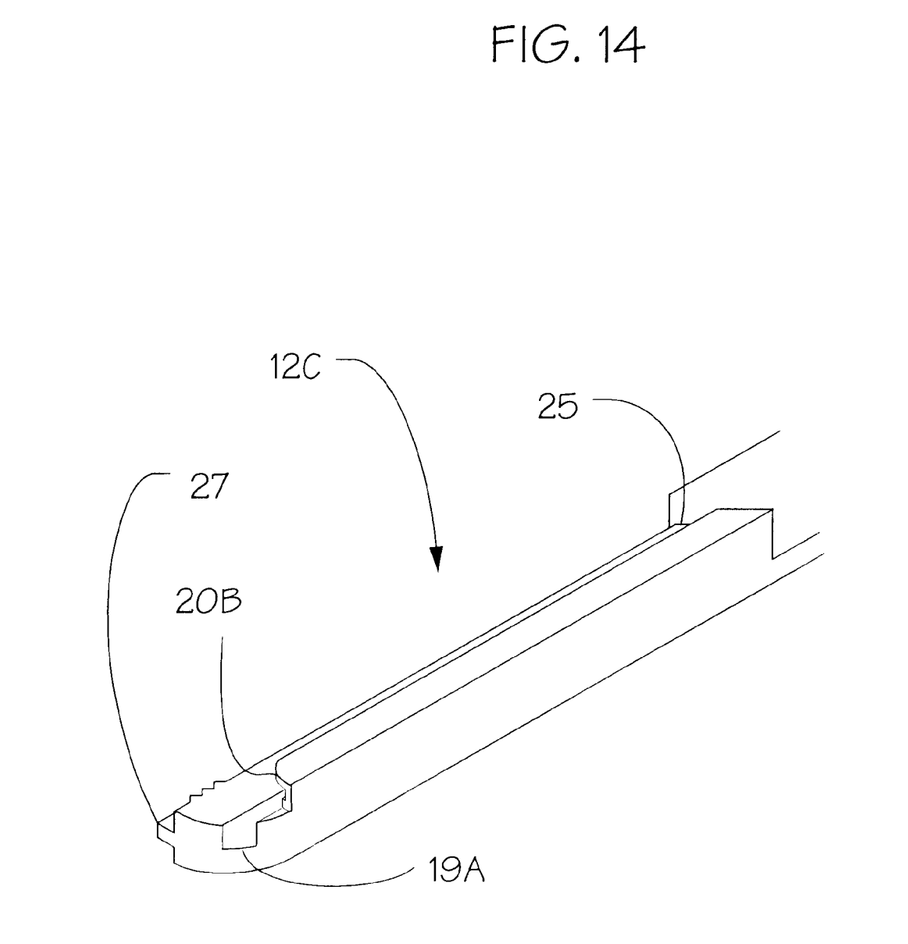
FIG. 14 is an enlarged view of jaw 12C of the tissue cutting clamp apparatus similar to FIG. 2.
Figure 16:
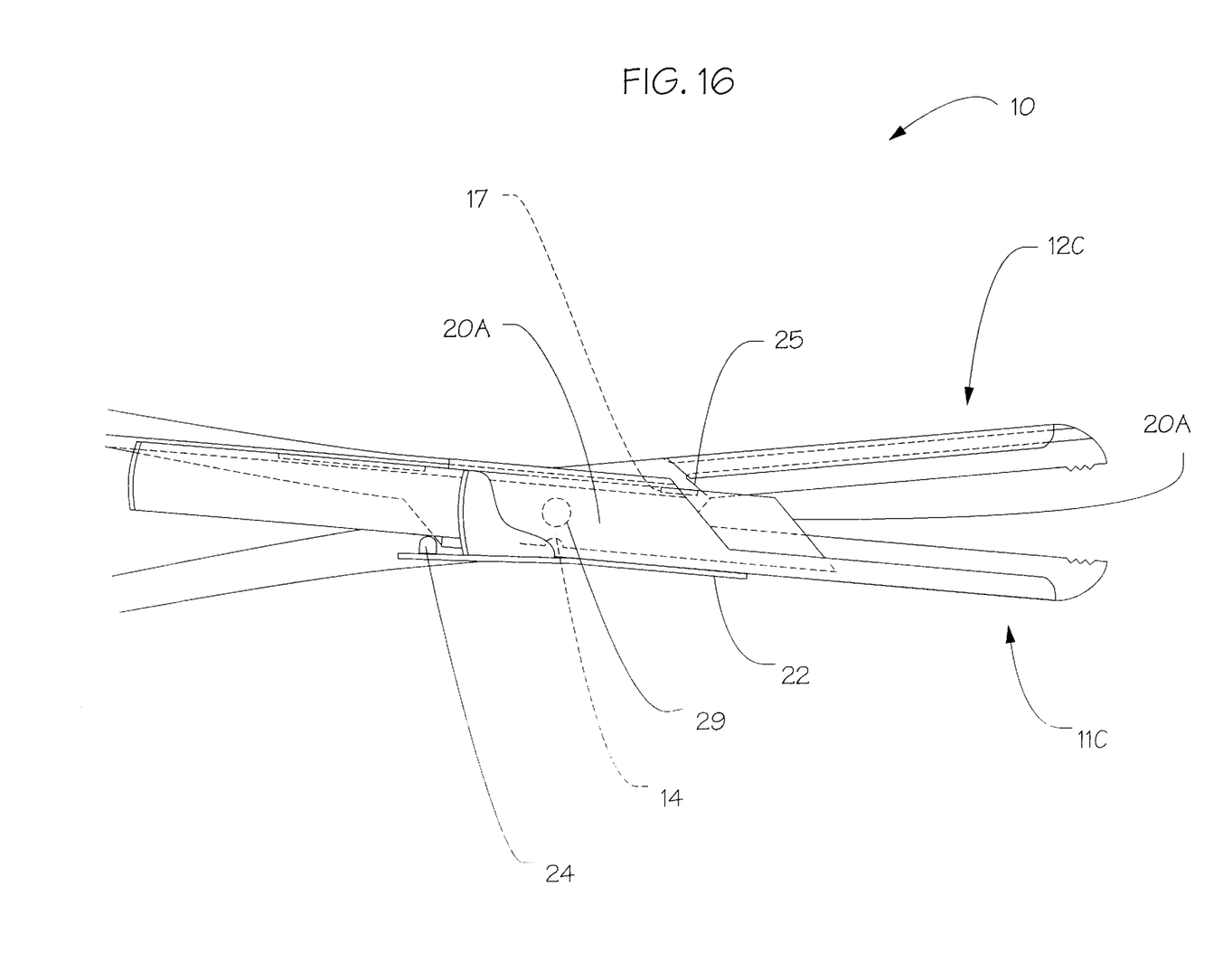
FIG. 16 is an enlarged view of jaws 11C and 12C of the tissue cutting clamp apparatus similar to FIG. 6.

As best shown in FIGS. 14 and 16, the reference numeral 25 depicts an obstruction portion of jaw 12C, which in combination with guide channel portion 19A precludes forward movement of the blade 13 when the jaws are partially open. In other words, with the jaws partially opened blade guide 17 will not be aligned to slide within channel portion 19A but rather will abut obstruction portion 25. The dimensions of guide 17, channel portion 19A and obstruction 25 can be varied to control the angle of opening of the jaws to where guide 17 will no longer abut obstruction 25.

For further assistance in retaining the blade, and for providing a tactile feel, a spring leaf member 22 has one end attached to the side of first clamping member 11 generally at a position corresponding to the start of the jaw area 11C. The free end of the leaf member 22 is provided with an inwardly facing projection 24, dimensioned, configured and arranged for engagement with the detent 14 in the edge of the blade 13 with the blade 13 fully retracted, and handle 16 abutting or adjacent stop member 21.

For limiting rearward or retracted movement of the blade 13, a stop member 21 is secured to the clamp member 11 intermediate pivot axis 29 and finger opening 11A, the position corresponding to the position of the blade as shown in FIG. 2, with the cutting edge 15 of the blade 13 within the shroud portion of the sheath 20A. In its retracted position (i.e. toward the finger gripping opening 11A), the blade 13 is in a no-interference position for clamping action.

The stop member 21 is basically an angle member having an end secured to the clamping member 11 with a surface extending inwardly at a transverse angle to the axial centerline of the member 11. The end of the leaf member 22 is provided with a bent portion overlying the upper surface of clamping member 11 to serve as a latch release handle to release the blade 13 for forward movement.

The jaws 11C and 12C are formed so that the faces thereof have interoperatively engaging tissue holding means, such as shown in FIGS. 2 and 3, the face of jaw 11c is formed with a shallow channel 26, with serrations 28 at the very end thereof, while the face of jaw 12C is formed with a mating rib 27, configured for being received within the channel 26 with the jaws in the closed position. FIGS. 1 and 4 depict the apparatus 10 with the jaws fully closed and the blade 13 in its operative cutting or forward position. FIG. 3 likewise shows the clamping members 11 and 12 separated, but with the blade 13 moved fully forward as assembled to the clamping member 11.

Figure 5:
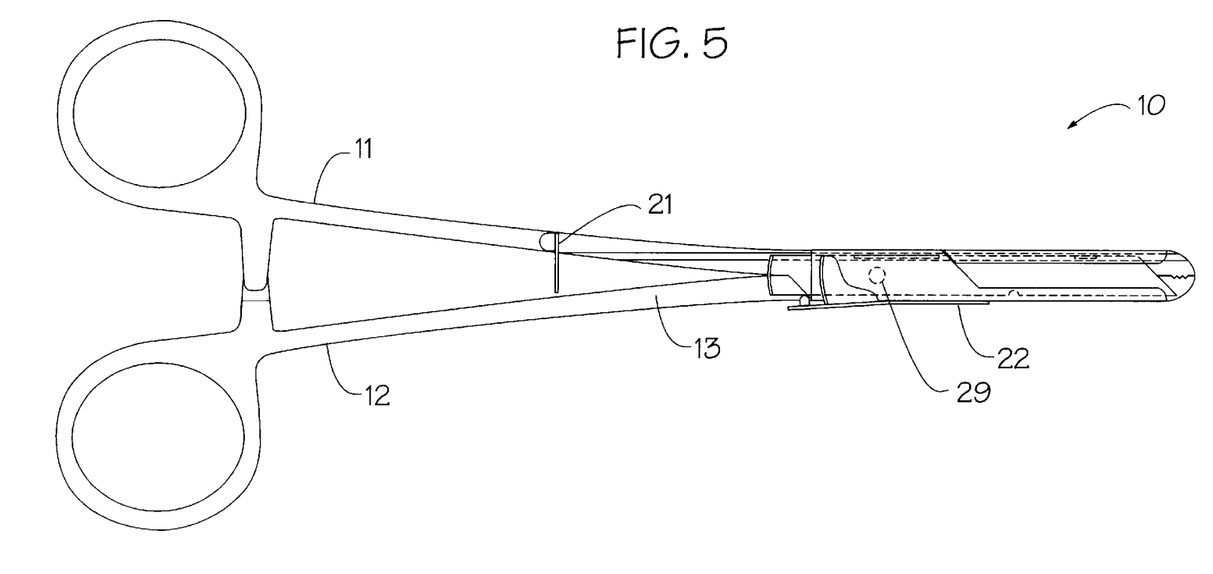
FIG. 5 is an end view of the tissue cutting clamp apparatus of FIG. 7 taken generally along line 5—5 thereof.
Figure 15:
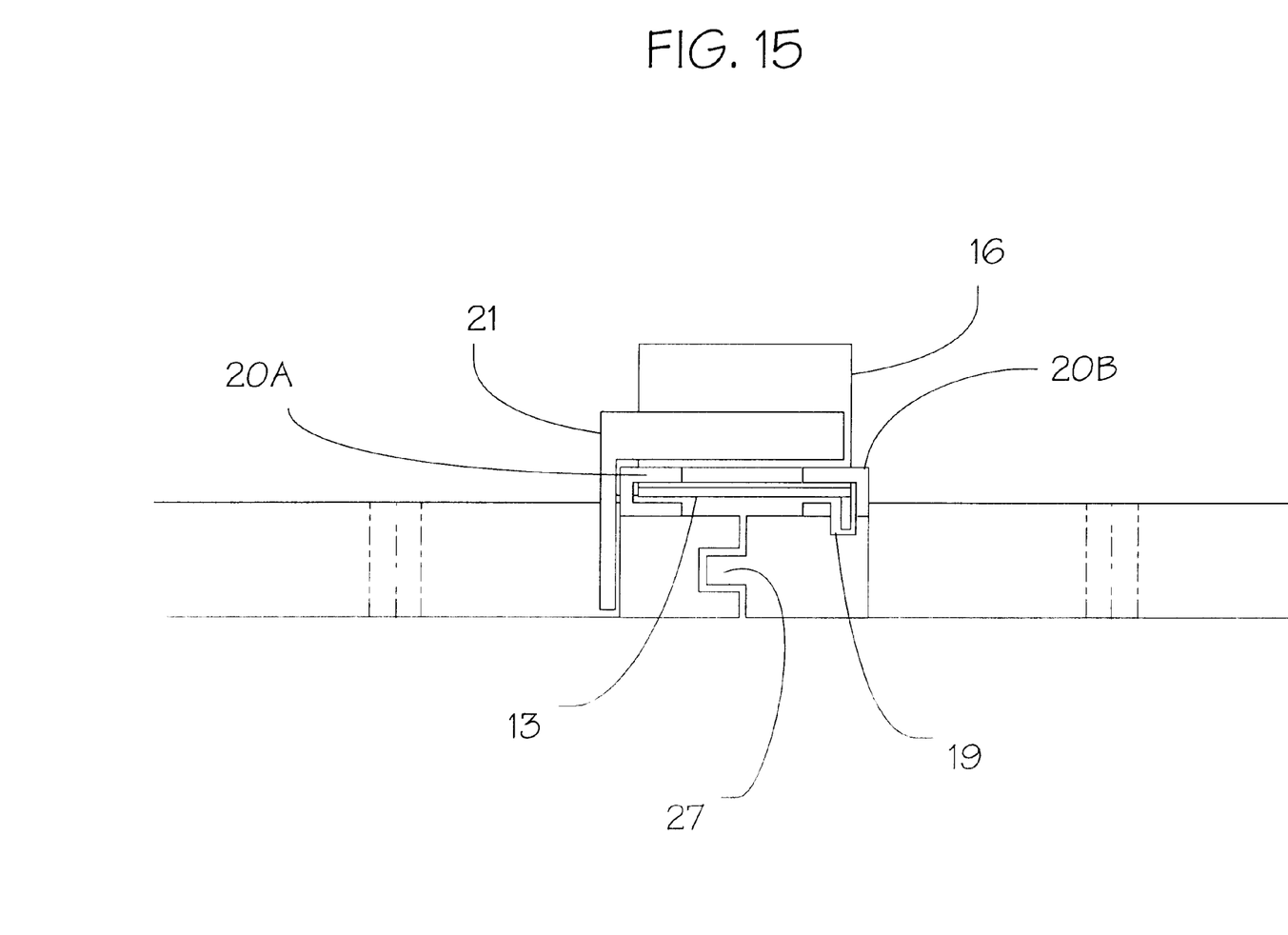
FIG. 15 is an enlarged view of the tissue cutting clamp apparatus as shown in FIG. 5.

As best depicted in FIGS. 5 and 15, in endwise view, the sheath construction can be best understood. As shown, the upper surfaces of the jaws 11C and 12C have portions which define a plane generally parallel to the plane of the blade 13, that is the blade 13 rides or slides over the plane of the upper surfaces of the jaws 11C and 12C. The opposing guide rails of sheaths 20A and 20B can be seen with the blade 13 therein, as well as the mating engaging jaw face portions.

Figure 6:
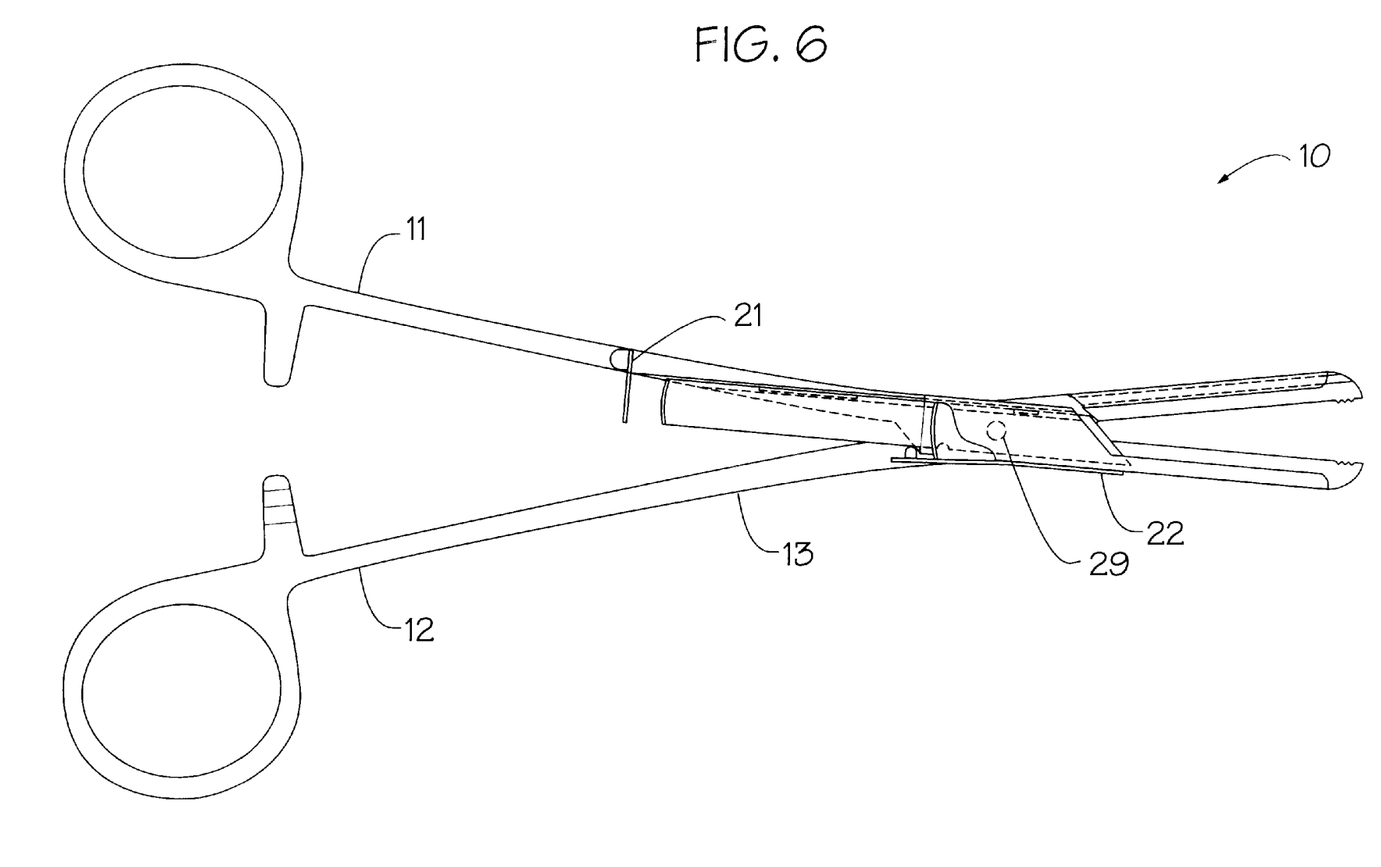
FIG. 6 is a plan view of the tissue cutting clamp apparatus of FIG. 1, shown in the open (unclamped) position with the blade in its retracted position with the jaws thereof in the open position prior to clamping.

FIGS. 6 and 16 show the apparatus 10 in the open position with the blade 13 almost fully retracted and, as can be seen, the sheath 20A and guide channel means on first clamping member 11 fully support the blade 13 in proper orientation. As shown, the blade 13 is not fully retractable inasmuch as the projection 24 of blade 13 is not detented in the detent 14.

However, as best shown in FIG. 16, the leading cutting edge 15 of the blade 13 is prevented from forward movement by the obstruction 25 formed in the jaw area 12C of clamping member 12, with the jaws partially opened just prior to clamping.

Figure 7:
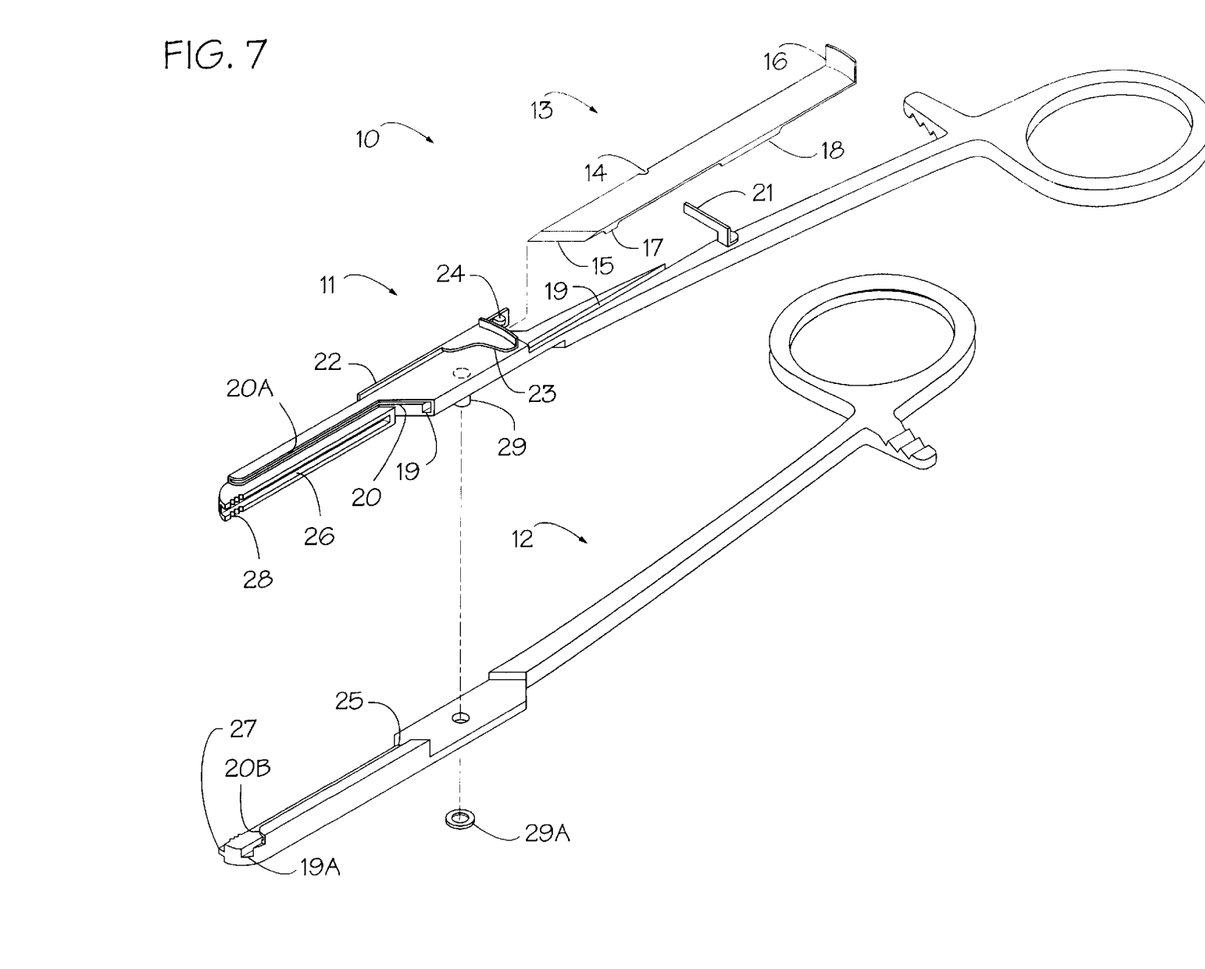
FIG. 7 is a plan view of the tissue cutting clamp apparatus of FIG. 1 with the blade in its retracted position with the jaws thereof in the closed position.
Figure 8:
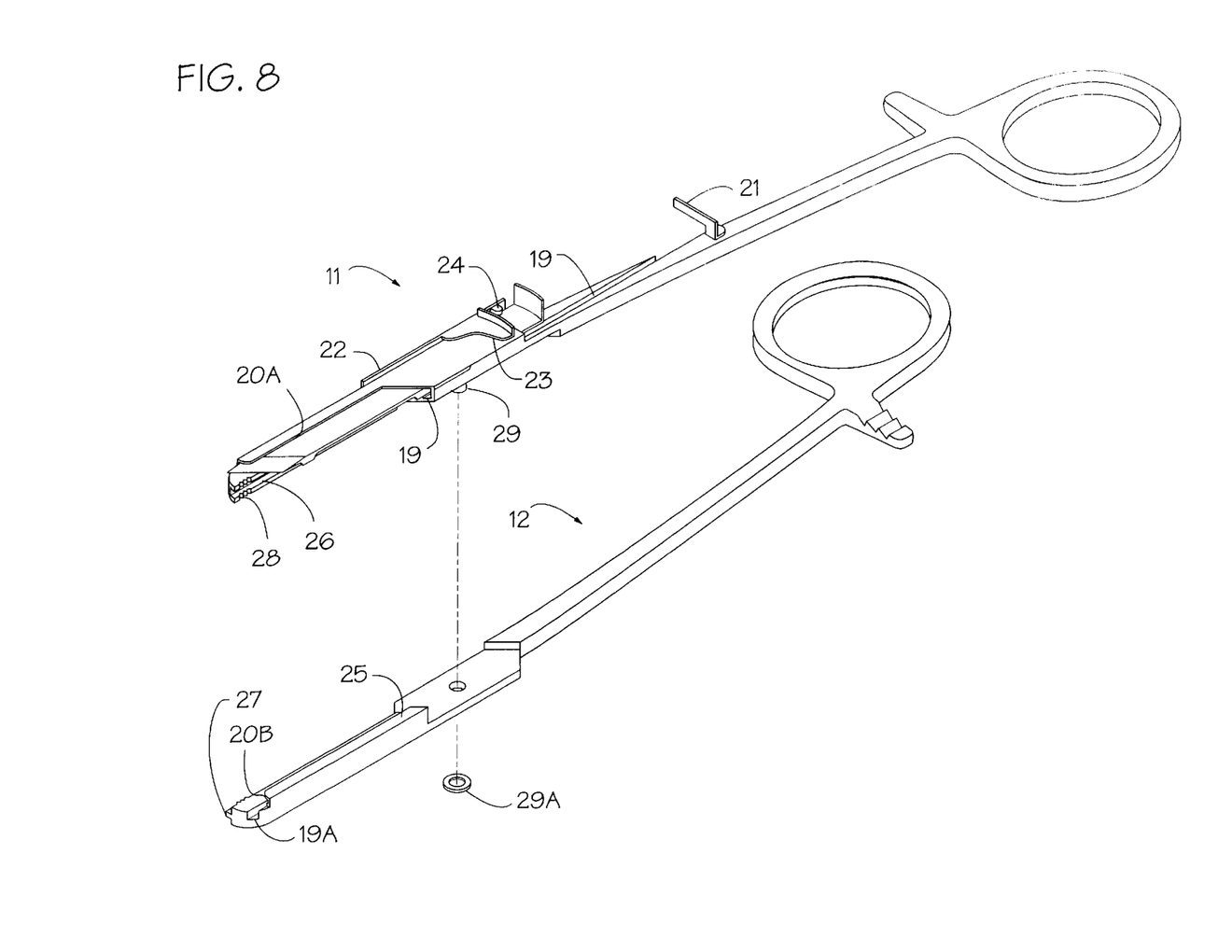
FIG. 8 is a side elevational view of the tissue cutting clamp apparatus of FIG. 7 as viewed downwardly relative to the plane of the drawing.
Figure 9:
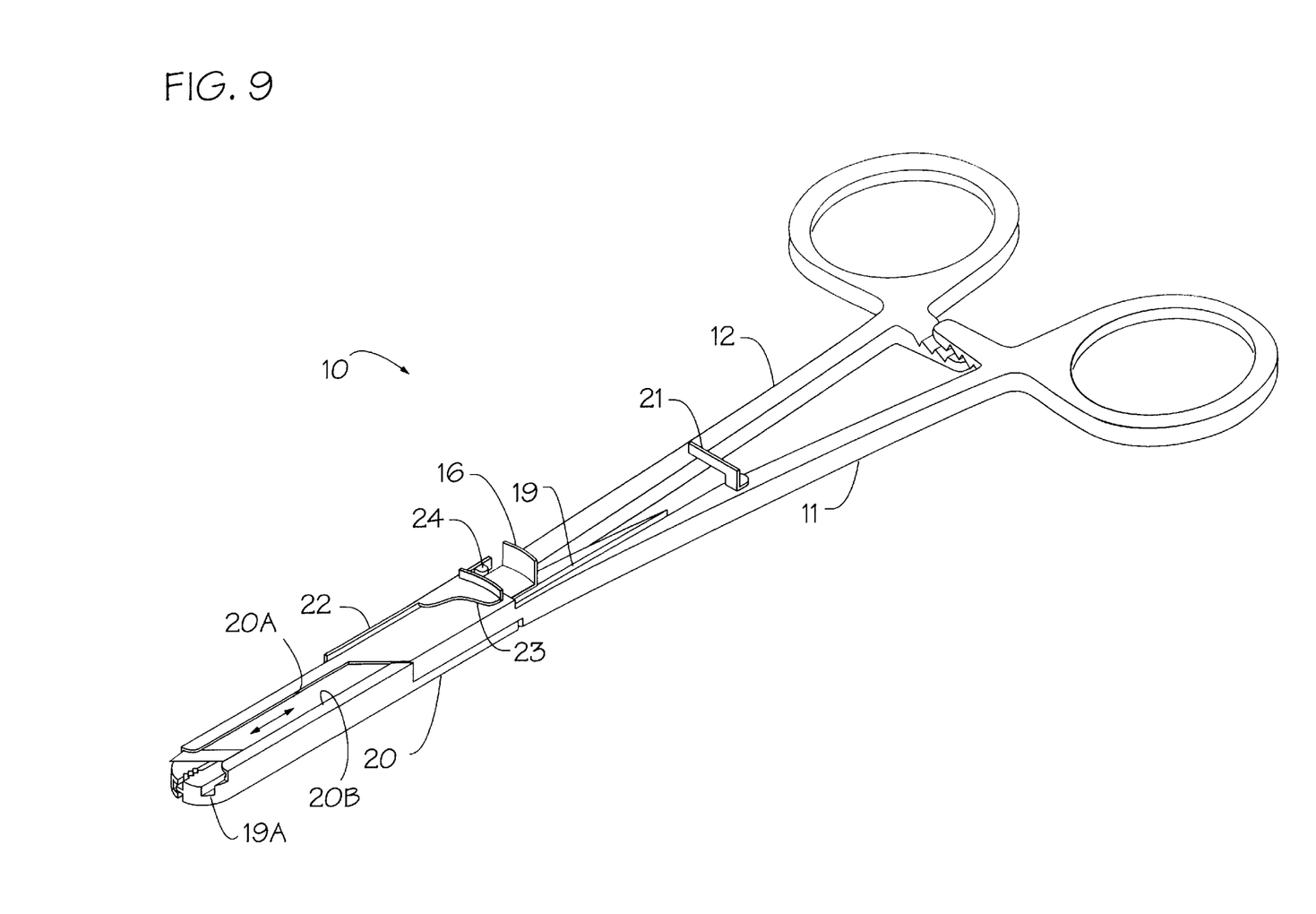
FIG. 9 is a side elevational view of the tissue cutting clamp apparatus of FIG. 7 as viewed upwardly relative to the plane of the drawing.

FIGS. 7 through 9 show the apparatus 10 with the jaws fully closed and the blade 13 fully retracted and detented. As can be seen the sheath guide rails are in generally parallel relation. The handle 16 of blade 13 abuts against stop 21 and the clamps are interlocked by virtue of the members 11B and 12B.

Figure 10:
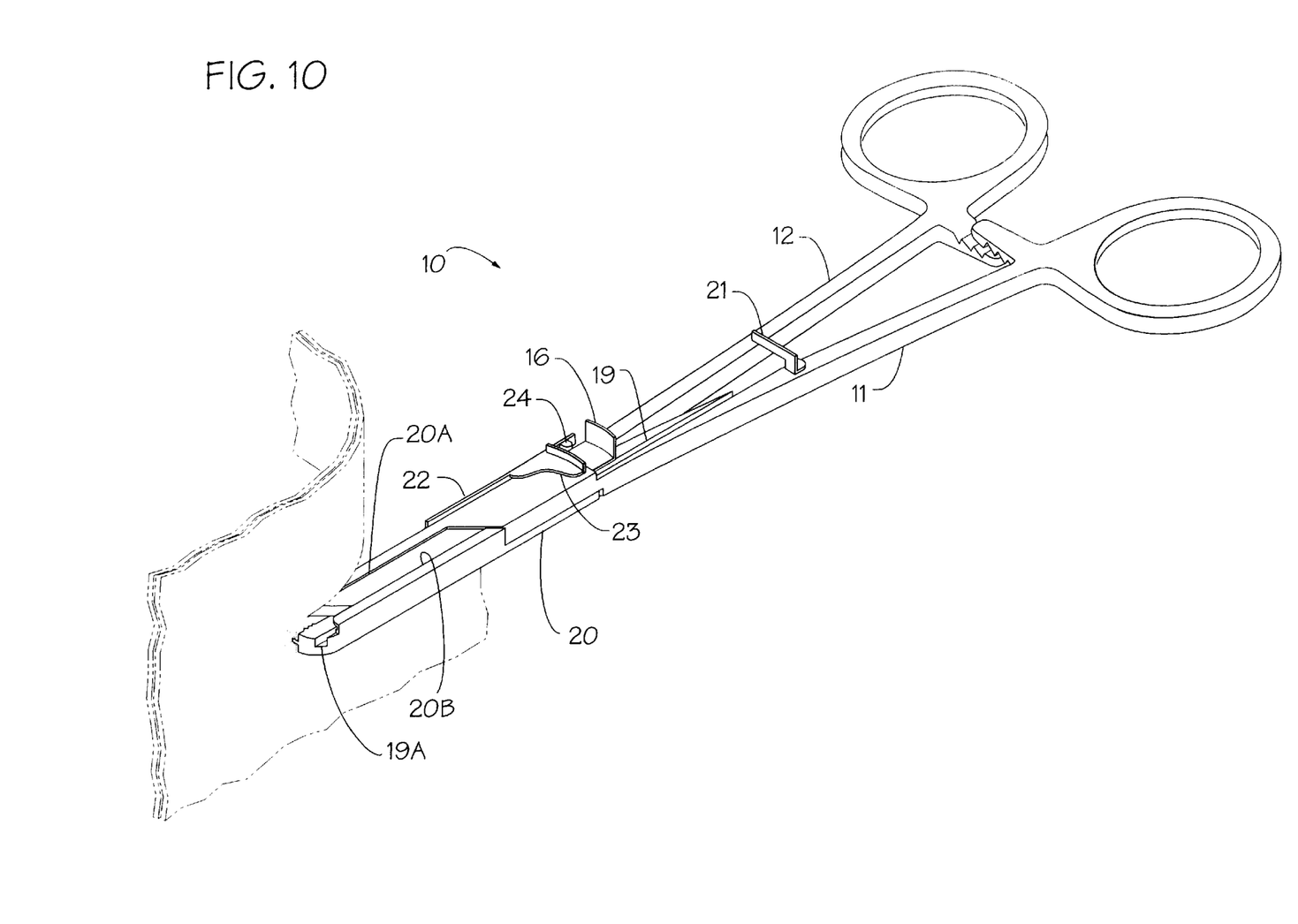
FIG. 10 is a perspective view of the first embodiment of the tissue cutting clamp apparatus in use in severing tissue.

FIG. 10 depicts the apparatus 10 in use cutting tissue 30. With the members 11 and 12 fully closed and locked, the handle 16 of the blade 13 is grasped, the latch 23 is pivoted against the bias of leaf spring member 22 to release the projection 24 from the detent 14 of the blade 13 and the handle 16 is moved forward to enable cutting of the clamped tissue 30.

Figure 11:
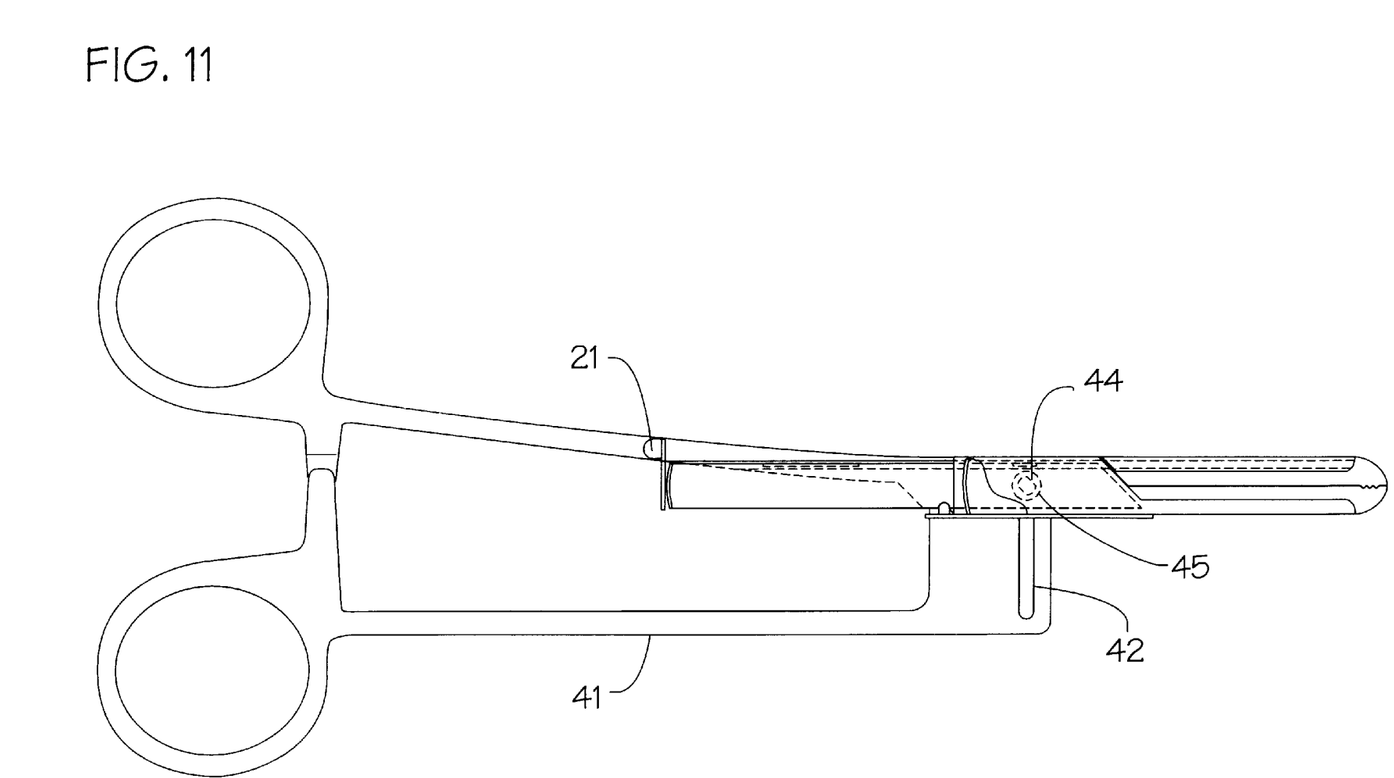
FIG. 11 is a plan view similar to FIG. 4 depicting an alternate embodiment of the tissue cutting clamp apparatus of FIG. 1, with the jaws in the closed position.
Figure 12:
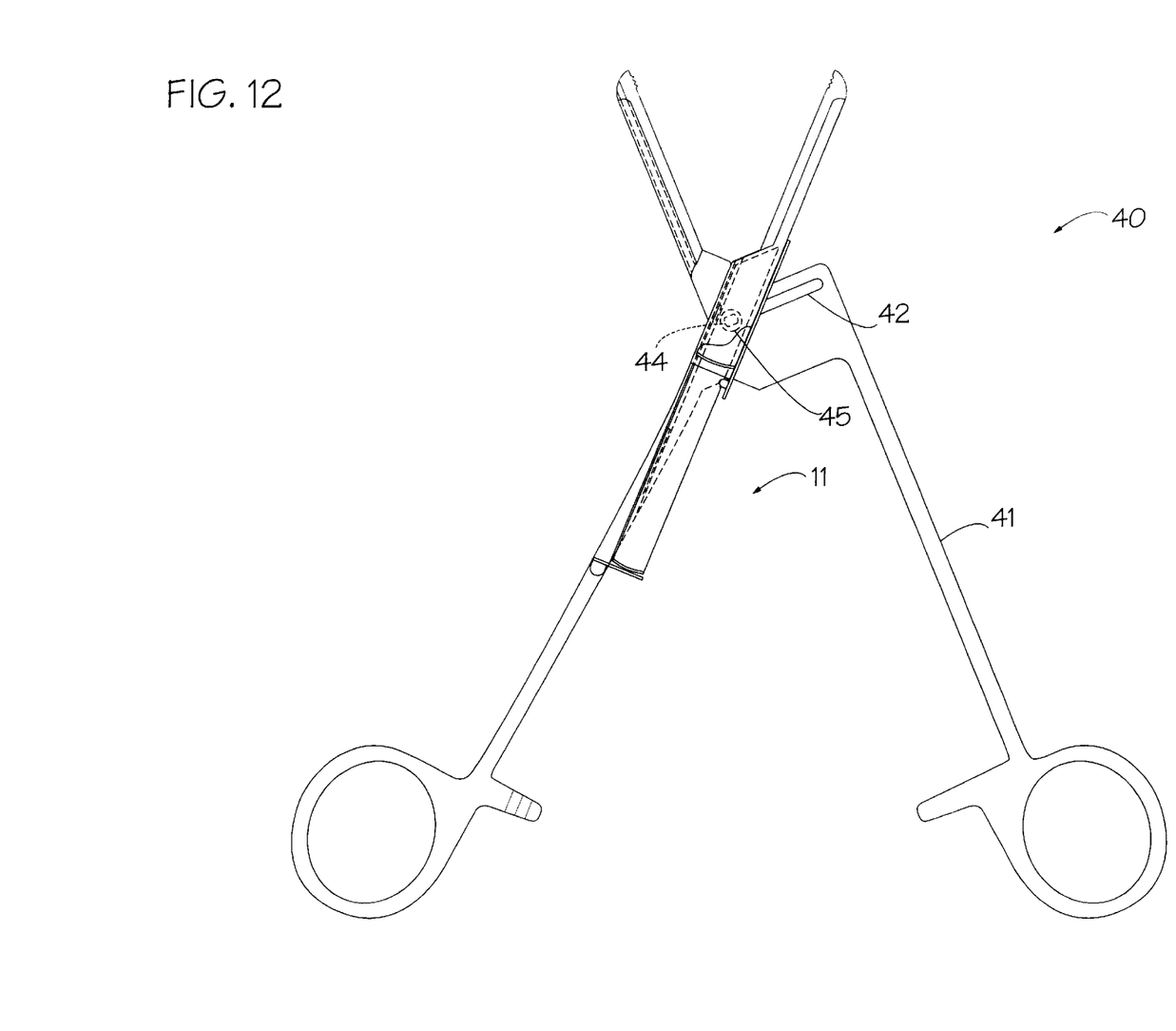
FIG. 12 is a plan view of the tissue cutting clamp apparatus of FIG. 11, with the jaws in the open position.
Figure 13:
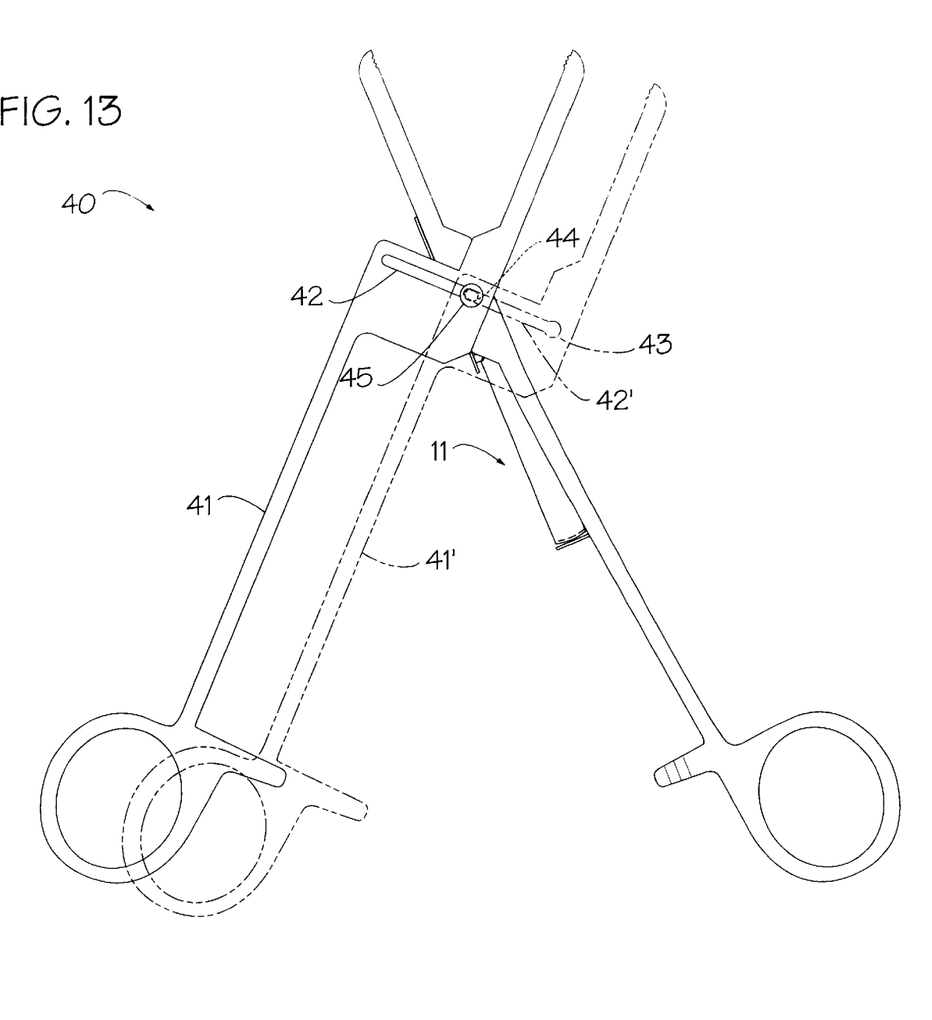
FIG. 13 is a plan view of the tissue cutting clamp apparatus similar to FIG. 12 with the jaws in the open position, and, showing in broken lines, the adjustable width aspect of the apparatus.

FIGS. 11 through 13 illustrate an alternative embodiment apparatus 40, in which the first clamping member 11 is configured identically as shown in FIGS. 1 through 10 and as previously described, along with the tissue cutting assembly means. However, the other clamping member 41 is provided with an enlarged, offset pivot portion 41A, which includes an elongate slot 42, through which passes the pivot connection member 44, the other end of which is held captive by a fastener 45. As shown in FIG. 12 the clamp apparatus 40, in its normal position, may be operated the same as the clamp apparatus 10 previously described.

However, as shown in FIG. 13, the clamping may be spatially separated by repositioning the clamping members 11 and 41 relative to one another to form a wider jaw opening, as depicted by the broken line depiction in which the like parts bear the same reference numerals followed by a prime ('). In the wider jaw opening positions, however, the tissue cutting is limited to a cut the width of the blade 13 along a line consistent with the movement of the blade, that is the tissue or body part will be notched as opposed to severed. Alternatively, a proportionally wider blade can be used.

In accordance with the present invention there has been shown and described a tissue cutting clamp apparatus of economical compact construction. The description using the directional terms forward, upper, etc., are not to be considered as limiting but are directional only in the sense that the so-described parts appear in the figures.

Although there has been shown and described a preferred embodiment, it is to be understood that other modifications may be made within the spirit and scope of the invention.

What is claimed is:

1. Hand manipulable tissue cutting apparatus formed in a scissors like configuration comprising:
    a first clamp member and a second clamp member with first and second respective jaws in opposing facing interoperative relation for clamping said tissue, with said clamp members pivotably coupled;
    an elongate generally planar blade having a cutting edge at one end thereof;
    sheath means on at least one of said clamp members for receiving said blade for movement therethrough to displace said cutting edge along a given plane generally perpendicular to said opposing face of said jaw of said at least one clamp member from a first position with said cutting edge in non-interference with said jaws to a second position overlying said jaws;
    said blade includes guide means depending therefrom and said sheath means has a guide channel formed as a recess therein for receiving said guide means and cooperating with said guide means for controlling movement of said blade along said given plane; and
    said at least one clamp member further includes latch means for releasably engaging said blade in said first position.

2. Hand manipulable tissue cutting apparatus formed in a scissors like configuration comprising:
    a first clamp member and a second clamp member with first and second respective laws in opposing facing interoperative relation for clamping said tissue, with said clamp members pivotably coupled;
    an elongate generally planar blade having a cutting edge at one end thereof;
    sheath means on at least one of said clamp members for receiving said blade for movement therethrough to displace said cutting edge alone a given plane generally perpendicular to said opposing face of said jaw of said at least one clamp member from a first position with said cutting edge in non-interference with said jaws to a second position overlying said jaws;
    said blade includes guide means and said at least one clamp member has a guide channel formed therein for receiving said guide means and cooperating with said guide means for controlling movement of said blade along said given plane;
    said at least one clamp member further includes latch means for releasably engaging said blade in said first position; and
    the other of said clamp members includes sheath means adjacent the jaw thereof, said sheath means of both said clamp members providing guide rail portions along the outside edges of both said jaws for passage of the blade therein with said jaws in the closed position.

3. The apparatus of claim 2 wherein adjacent surfaces of said jaws in the closed position define a plane generally perpendicular to the plane of mating of said jaws and wherein said blade moves in a plane generally parallel to and in proximate relation with the said plane generally perpendicular to the plane of mating of said jaws.

4. The apparatus of claim 3 wherein the other of said clamp members includes sheath means adjacent the jaw thereof, said sheath means of both said clamp members providing guide rail portions along the outside edges of both said jaws for passage of the blade therein with said jaws in the closed position.

5. Hand manipulable tissue cutting apparatus formed in a scissors like configuration comprising:
    a first clamp member and a second clamp member with first and second respective jaws in opposing facing interoperative relation for clamping said tissue, with said clamp members pivotably coupled;
    an elongate generally planar blade having a cutting edge at one end thereof;
    sheath means on at least one of said clamp members for receiving said blade for movement therethrough to displace said cutting edge along a given plane generally perpendicular to said opposing face of said jaw of said at least one clamp member from a first position with said cutting edge in non-interference with said jaws to a second position overlving said jaws;
    said blade includes guide means and said at least one clamp member has a guide channel formed therein for receiving said guide means and cooperating with said guide means for controlling movement of said blade along said given plane;
    said at least one clamp member further includes latch means for releasably engaging said blade in said first position; and
    said blade includes detent means formed in a side edge thereof and said latch means includes a spring biased projection for engaging said detent means with said blade in said first position and a portion overlying the upper surface of said at least one clamp member providing means for opposing said spring bias to manually release said blade from said detent.

6. The apparatus of claim 5 wherein said blade further includes an upwardly extending portion opposite said cutting edge for manual gripping to enable movement of said blade, and said at least one clamp member further includes a stop member in generally proximate relation to said extending portion with said blade in said first position.

7. The apparatus of claim 5 wherein said clamp members have adjustable pivot means for enabling changing the spacing between said jaws.

8. Hand manipulable tissue cutting apparatus formed in a scissors like configuration comprising:

a first clamp member and a second clamp member with first and second respective jaws in opposing facing interoperative relation for clamping said tissue, with said clamp members being pivotably coupled;

an elongate generally planar blade having a cutting edge at one end thereof;

first sheath means on said first clamp member for receiving said blade for movement therethrough to displace said cutting edge along a given plane generally perpendicular to the plane of the mating faces of said jaws from a first position with said cutting edge in non-interference with said jaws to a second position overlying said jaws; and said second clamp member includes second sheath means adjacent the jaw thereof, said first and second sheath means providing cooperating guide rail portions along the outside edges of both said jaws for passage of the blade therein with said jaws in the closed position.

9. The apparatus of claim 8 wherein said blade includes detent means formed in a side edge thereof and said first clamp member includes spring biased latch means for releasably engaging said detent means with said blade in said first position.

10. The apparatus of claim 9 wherein said latch means includes a spring biased projection for engaging said detent means with said blade in said first position and a bent portion overlying the upper surface of said at least one clamp member providing means for opposing said spring bias to manually release said blade from said detent.

11. The apparatus of claim 9 wherein said blade includes guide means formed on the other side edge thereof and said first clamp member includes a guide channel formed in the surface thereof for cooperating with said guide means for controlling movement of said blade along said given plane.

12. The apparatus of claim 9 wherein said first sheath provides a protective shroud for said cutting edge in said first position.

13. The apparatus of claim 9 wherein said blade further includes an upwardly extending portion opposite said cutting edge for manual gripping to enable movement of said blade, and said first clamp member further includes a stop member in generally proximate relation to said extending portion with said blade in said first position.

14. The apparatus of claim 10 wherein the jaw of said second clamp member includes a blade guide channel in general alignment with the guide channel of said first clamp member with said jaws fully closed.

15. The apparatus of claim 14 wherein said second clamp member further includes an obstruction adjacent the entrance end of said guide channel for deterring movement of said blade to said second position with said jaws in an open position.

16. The apparatus of claim 10 wherein said clamp members have adjustable pivot means for enabling changing the spacing between said jaws.

17. A method for clamping and cutting body tissue comprising the steps of:

clamping said tissue with first and second manually operable clamp means having respectively first and second jaws in opposing facing interoperative relation, said jaws pivotably coupled in a scissors like configuration with said first clamp means including first sheath means on the upper surface thereof for slidably receiving an elongate generally planar blade for movement therethrough, said blade having a cutting edge at the forward end thereof, and said second clamp means including second sheath means adjacent the jaw thereof, said first and second sheath means providing cooperating guide rail portions along the outside edges of both said jaws for passage of the blade therein with said jaws in the closed position;

cutting the clamped tissue by moving said cutting edge from a first position with said cutting edge in non-interference with said jaws to a second position overlying said jaws along a plane generally perpendicular to the mating faces of said jaws.

18. The apparatus of claim 1 wherein said blade includes detent means formed in a side edge thereof and said at least one clamp member includes spring biased latch means for releasably engaging said detent means with said blade in said first position, said latch means including a spring biased projection for engaging said detent means with said blade in said first position and a bent portion overlying the upper surface of said at least one clamp member providing means for opposing said spring bias to manually release said blade from said detent.

19. The apparatus of claim 1 wherein said blade further includes an upwardly extending portion opposite said cutting edge for manual gripping to enable movement of said blade, and said at least one clamp member further includes a stop member in generally proximate relation to said extending portion with said blade in said first position.

20. The apparatus of claim 1 wherein said second clamp member further includes an obstruction adjacent the entrance end of said guide channel for deterring movement of said blade to said second position with said jaws in an open position.

* * * * *